United States Patent [19]
Larsson

[11] Patent Number: 4,964,851
[45] Date of Patent: Oct. 23, 1990

[54] BATTERY-POWERED BREASTPUMP

[75] Inventor: Karl O. A. H. Larsson, Zug, Switzerland

[73] Assignee: ISG/AG, Zug, Switzerland

[21] Appl. No.: 328,106

[22] Filed: Mar. 23, 1989

[51] Int. Cl.⁵ .............................................. B61M 1/06
[52] U.S. Cl. ..................................... 604/74; 604/248; 604/346
[58] Field of Search ................................... 604/74–76, 604/118, 119, 248, 346; 119/14.32, 14.33, 14.53; 137/533.19

[56] References Cited

U.S. PATENT DOCUMENTS 1,596,520  8/1926  Eskholme et al. .
3,931,795  1/1976  Duncan .
4,263,912  4/1981  Adams .
4,673,388  4/1984  Schlensog et al. .
4,857,051  8/1989  Larsson ................................ 604/74

FOREIGN PATENT DOCUMENTS

158976   5/1957  Denmark .
2082920  3/1980  United Kingdom .
2127293  4/1984  United Kingdom .

Primary Examiner—Stephen C. Pellegrino
Attorney, Agent, or Firm—Willian Brinks Olds Hofer Gilson & Lione

[57] ABSTRACT

An electrically-powered breastpump is disclosed that includes a suction bell, battery-operated suction unit, and a receiving container. The pump includes a rotatable valve that directs the suction of the pump in alternating fashion between the suction bell and the receiving container.

30 Claims, 4 Drawing Sheets

FIG. 1

BATTERY-POWERED BREASTPUMP

BACKGROUND OF THE INVENTION

This invention relates to breastpumps, particularly motorized breastpumps for drawing breast milk.

Breastpumps are convenient for nursing mothers, because, among other things, they allow the nursing mother to draw off breast milk to feed to the child at a later time when the mother may not be present. For some mothers, breastpumps are required, particularly when the child has sucking difficulties or if the mother has problems with excessive or deficient milk production, or cannot empty completely. Some mothers also require breastpumps in the event of soreness or injury of the mammilla, or sunken mammilla.

Manual breastpumps are commonplace, primarily because they are inexpensive and easy to manufacture. However, the pressure produced by manual breastpumps can be very uneven. Particularly if they are operated improperly, the pressure can be insufficient to draw off sufficient milk, or can be excessively high, placing an inordinate strain on the skin of the breast. Some motorized breastpumps have been proposed, but have been too large and expensive.

Thus, for motorized breastpumps to compete effectively in the marketplace, they must be lightweight, portable, yet achieve good pressure regulation in defined limits, for example, between 100 and 220 millimeters of mercury (mmHg).

SUMMARY OF THE INVENTION

The present invention is a lightweight, inexpensive and portable breastpump that achieves good pressure regulation. A preferred pump according to this invention includes a suction bell, a container for receiving fluid from the suction bell, and a battery-operated suction pump for creating reduced pressures in the suction bell and in the container. A rotatable valve exposes the suction bell and container in alternating fashion to reduced pressures, exposing the suction bell to reduced pressure during the time when the container is at atmospheric pressure and exposing the container to reduced pressure while the suction bell is at atmospheric pressure. Finally, a pressure responsive valve member is disposed between the bell and container to open when the container pressure is lower than the pressure in the bell to allow milk collected in the bell to drop into the container.

Other features and advantages of the present invention will become apparent from the detailed description that follows taken in conjunction with the drawings, in which:

BRIEF DESCRIPTION OF THE DRAWINGS

FIG. 3 is a cross-section taken along the plane of line 3—3 of FIG. 2;

DETAILED DESCRIPTION OF A PREFERRED EMBODIMENT

A breastpump 20 of the current invention includes a suction bell 22 that is placed on the breast for drawing milk. A reduced pressure in the suction bell is generated by a suction drive unit 24. Milk drawn from the breast is collected in a collection container 26.

Suction bell 22 includes a bell portion 28 to contact with the breast and a neck portion 30. The lower end of neck 30 is inside container 26 and includes a flapper (pressure responsive) valve 32 as disclosed in co-pending U.S. Pat. application No. 07/278,047 filed Nov. 30, 1988 that is incorporated herein by reference. Neck portion 30 also includes an annular threaded collar 34 that threads onto the open end 36 of container 26. Suction bell 22 also includes a cylindrical portion 38 that receives the cylindrical end 40 of suction drive unit 24.

Suction drive unit 24 includes a suction pump assembly 42 (FIGS. 2 and 8), a rotatable valve assembly 44, and a motor 46 for driving the rotatable valve assembly 44 and suction pump assembly 42. Suction pump assembly 42, rotatable valve assembly 44, and a motor 46 are positioned within a two-piece housing formed from cylindrical end 40 and a rear housing portion 48.

Suction pump assembly 42 has a membrane 50 located between a top plate 52 (FIGS. 2 and 8) and a membrane deck 54. Membrane deck 54 has a horizontal portion 56 and a vertical portion 58, membrane 50 being sandwiched between the horizontal portion 56 and top plate 52. Membrane 50 includes a pumping diaphragm portion 60 (FIGS. 1 and 2) disposed within a circular opening 62 through horizontal portion 56 of membrane deck 54. A pumping chamber 64 (FIGS. 1 and 2) is formed between pumping diaphragm 60 and top plate 52.

Pumping diaphragm 60 is reciprocated into and out of pumping chamber 64 by a sleeve bearing 66 (FIGS. 2 and 8) that includes a driver arm 68 that is connected to and received within a cylindrical portion 70 of pumping diaphragm 60. Bearing 66 has an opening 72 that receives an enlarged diameter portion 74 of an eccentrically mounted cam 76 mounted on the drive shaft 78 of motor 46. As drive shaft 78 is rotated by motor 46, eccentric cam 76 rotates enlarged diameter portion 74 such that bearing 66 reciprocates driver arm 68, imparting reciprocal motion to pumping diaphragm 60 to expand and contract pumping chamber 64.

Figure 1:
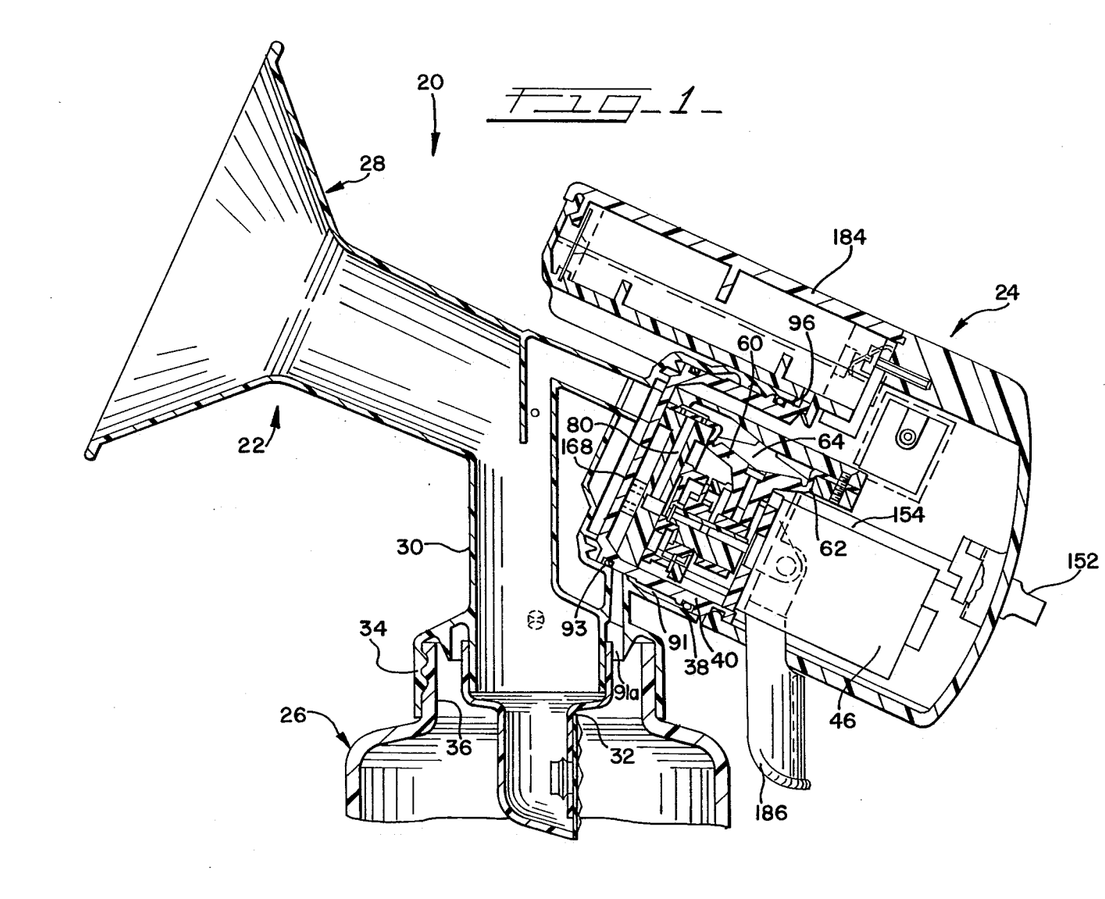
FIG. 1 is a longitudinal cross-sectional view of a breastpump made in accordance with the present invention.
Figure 5:
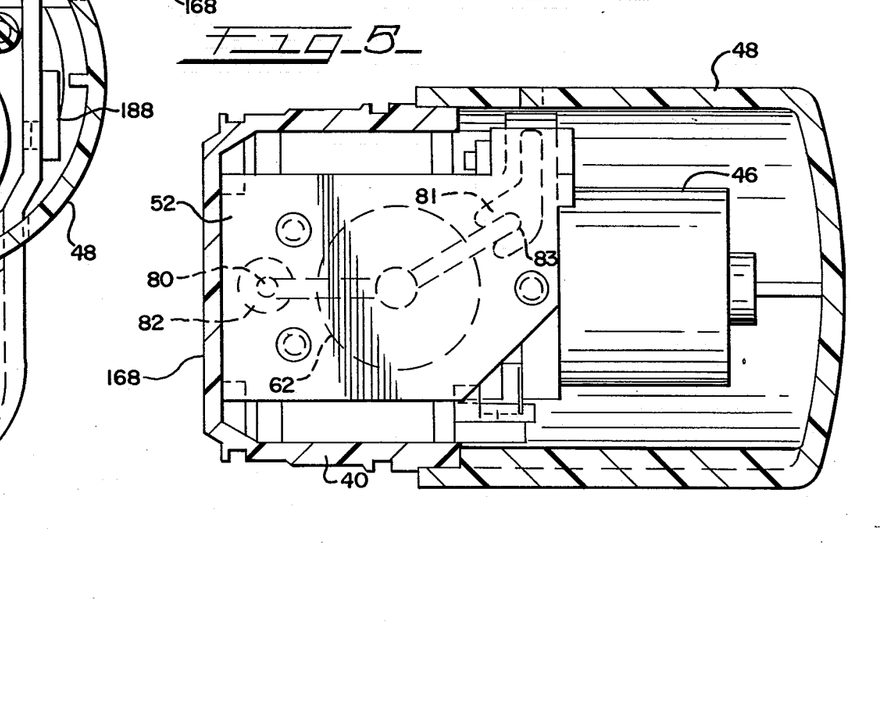
FIG. 5 is a cross-section taken along the plane of line 5—5 of FIG. 2.
Figures 6, 7, 8:
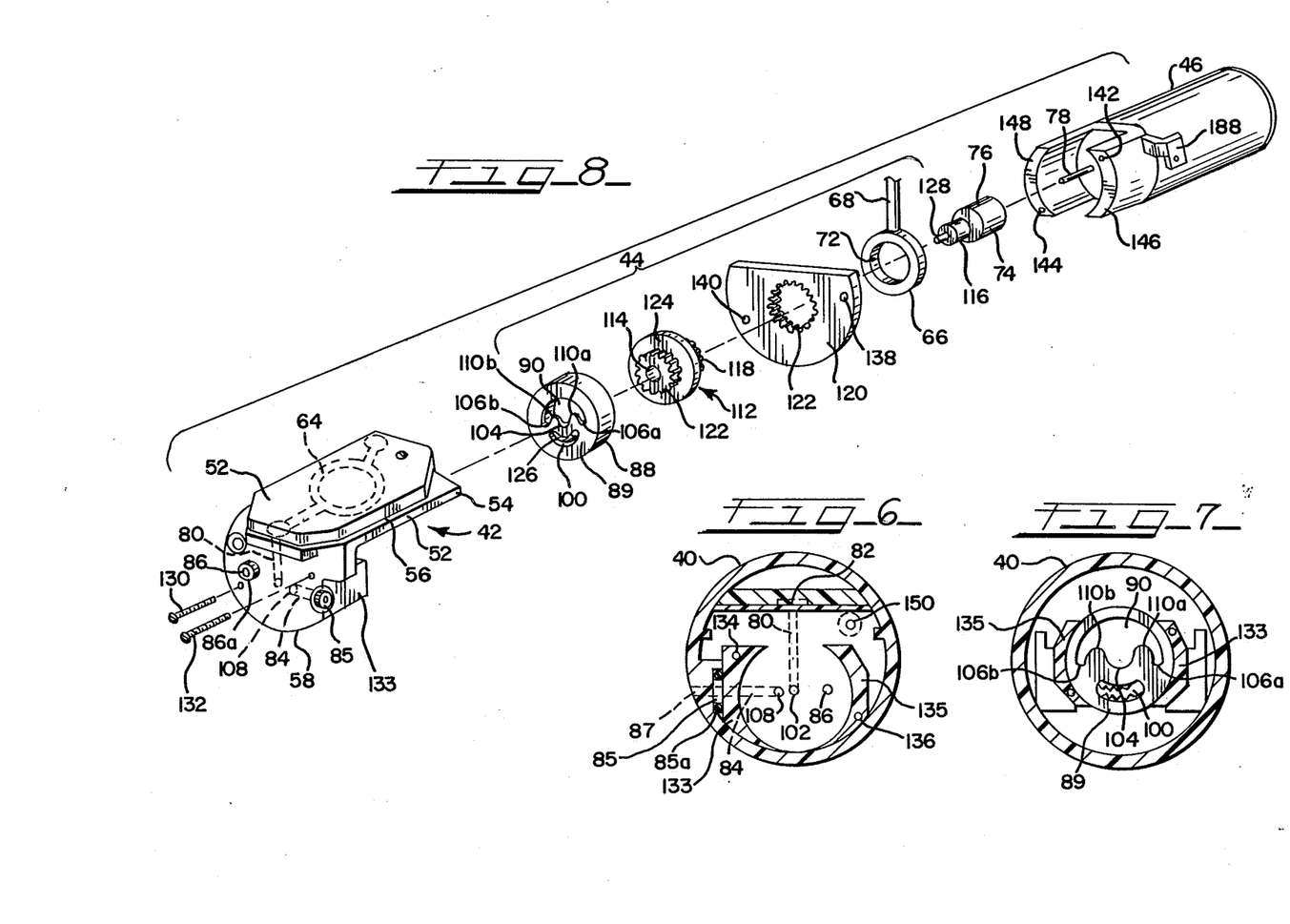
FIG. 6 is a cross-section taken along the plane of line 6—6 of FIG. 2.
FIG. 7 is a cross-section taken along the plane of line 7—7 of FIG. 2.
FIG. 8 is an exploded perspective view of the vacuum pump assembly, rotatable valve assembly, and motor of the drive unit.

On an intake (expansion) stroke, pumping diaphragm 60 is drawn downwardly by driver arm 68, and air is drawn from either suction bell 22 or container 26 (as governed by rotatable valve assembly 44) through a passage 80 (FIGS. 1, 6 and 8). As air is drawn into pumping chamber 64 through passage 80, a flapper valve 82 is drawn upwardly from the upper end of passage 80 to permit air to be drawn from either the container or the suction bell through passage 80. At the same time, a corresponding pumping chamber outlet flapper valve 81 (FIG. 5) is urged into position across an outlet 83 from the pumping chamber to prevent air from being drawn through outlet 83 into the pumping chamber during the intake stroke.

As rotating cam 76 continues its rotation, it urges driver arm 68 upwardly, forcing pumping diaphragm 60 inwardly of pumping chamber 64 to force air out of pumping chamber 64 past outlet flapper valve 83 that opens when pumping chamber 64 is pressurized. As pumping chamber 64 pressurizes on the exhaust stroke, inlet flapper valve 82 is urged against the upper end of passage 80, preventing pressurized air from being introduced into suction bell 22 or collection container 26 through passage 80.

The suction drawn by suction pump assembly 42 through passage 80 is diverted in an alternating fashion by rotatable valve assembly 44 between two passages through vertical portion 58: a passage 84 (FIGS. 6 and 8) that communicates with the inside of container 26, and a passage 86 that extends through vertical portion 58 to establish communication between passage 80 and bell 22.

Passage 84 communicates with the inside of the container as follows. Passage 84 terminates at its distal end in a stud 85 (FIGS. 6 and 8) that extends from the side of vertical portion 58. Stud 85 abuts against the inside of cylindrical end 40 (FIG. 6) so that an opening 87 through cylindrical end 40 aligns with passage 84. A washer 85a of a resilient material is positioned around stud 85 between a support 133 (FIG. 6) and the inside of cylindrical end 40 to seal the juncture between passage 84 and opening 87 against a suction being drawn on the inside of cylindrical end 40.

Opening 87 is positioned in an annular space 91 (FIG. 1) formed between the outside of cylindrical end 40 and the inside of cylindrical portion 38. Annular space 91 is sealed from the pressure inside bell 22 by an O-ring 93 (FIG. 1) located in a groove 95 around cylindrical end 40. Annular space 91 is sealed from the atmospheric pressure outside breast pump 20 by an O-ring 96 located between cylindrical end 40 and cylindrical portion 38. A passage 91a (FIG. 1) through cylindrical portion 38 establishes communication between annular space 91 and the inside of annular portion 34 so that suction drawn on annular space 91 through passage 84 will be drawn on the inside of container 26.

Passage 86 passes through vertical portion 58, and through a stud 86a (FIGS. 2 and 8) extending forward from vertical portion 58 and through face 168 of cylindrical portion 40. Suction drawn through passage 86 is thereby drawn on suction bell 22.

A rotatable disk valve 88 of rotatable valve assembly 44 (FIGS. 2, 7 and 8) controls the diversion of suction between the collection container 26 and the suction bell 22. Disk valve 88 includes a flat face 89 with a generally semi-circular recess 90. An arcuate opening 100 extends completely through disk valve 88. When assembled (FIG. 2), flat face 89 (FIGS. 7 and 8) sealingly abuts the rear surface of vertical portion 58 (a diverter plate) of membrane deck 54. The lower end 102 of passage 80 (FIGS. 2 and 6) aligns with a central projection 104 of recess 90. The distance between lower end 102 and passage 86 is roughly equal to the distance between central projection 104 and two side projections 106a and 106b (FIGS. 7 and 8) of recess 90 such that as rotatable valve 88 rotates, suction drawn through passage 88 will draw a suction through passage 86 when recess 90 is rotating past passage 86 between side projections 106a and b. Accordingly, suction will be drawn on suction bell 22 as passage 86 is aligned with recess 90.

When recess 90 is not aligned with passage 86, passage 86 is first occluded briefly by a portion of flat face 89 between a projection 106a or 106b (depending on the rotational direction of motor 46) and arcuate opening 100. When passage 86 is occluded after suction has been drawn through it, the reduced pressure within suction bell 22 is briefly held until the rotation of disk valve 88 brings arcuate opening 100 into alignment with passage 86. At this time, passage 86 is exposed to atmospheric pressure in housing 48 that releases the suction in suction bell 22 until suction is drawn again when recess 90 rotates into alignment with passage 86.

Suction is drawn on collection container 26 when recess 90 is aligned with the proximal end 108 (FIGS. 6 and 8) of passage 84. The distance between the proximal end 108 of passage 84 and the lower end 102 of passage 80 is approximately the same as the radial distance between central projection 104 and either of the two side projections 110a and 110b of flat face 89, which projections 110a and 110b project into recess 90. In other words, suction is drawn through passage 84 (and thus container 26) when recess 90 is aligned with proximal end 108 along an arcuate path between projections 110 a and b of flat face 89.

Collection container 26 is exposed to atmospheric pressure when proximal end 108 is aligned with arcuate opening 100. However, the suction drawn on container 26 while recess 90 is aligned with proximal end 108 is not held in container 26. Flapper (pressure responsive) valve 32 opens when a suction is drawn on container 26, allowing the milk to drop from the neck 30 of suction bell 22 into the container.

Because the arcuate distance in recess 90 between side projections 106a and 106b is longer than the arcuate distance in recess 90 between side projections 110a and b, the suction drawn on suction bell 22 will be longer in time and can be stronger than the suction drawn on collection container 26. The strength of the suction drawn on suction bell 22 can be regulated by a regulator valve described below.

Disk valve 88 is rotated by epicyclic gear 112 (FIGS. 2 and 8) of rotatable valve assembly 44. Epicyclic gear 112 includes a cylindrical opening 114 along its longitudinal axis. Opening 114 receives an eccentrically-mounted reduced diameter portion 116 of eccentric cam 76. Thus, as eccentric cam 76 is rotated by motor 46, epicyclic gear 112 will rotate around the longitudinal axis of motor shaft 78 as well. Epicyclic gear 112 includes a first gear portion 118 (FIG. 2) that is received within and driveably engages a stationary gear 120 that has an annular gear 122 of a diameter larger than the diameter of first gear portion 118. As eccentric cam 76 rotates gear 112, epicyclic motion is imparted to gear 112 as the gear teeth on first gear portion 118 driveably engage annular gear 122 of stationary gear 120.

Epicyclic gear 112 also includes a second gear portion 122 (FIGS. 2 and 8) separated from first gear portion 118 by a radial flange 124. Second gear portion 122 driveably engages an annular gear 126 (FIG. 2) positioned on the side of rotatable valve 88 opposite flat face 89. The diameter of second gear portion 122 is smaller than the diameter of annular gear 126. However, the diameter of second gear portion 122 is larger than the diameter of first gear portion 118 (see FIG. 2).

Disk valve 88 is mounted on a stud 128 (FIG. 2) that is mounted on the distal end of eccentric cam 76 such that the longitudinal axis of stud 128 is coincident with the longitudinal axis of drive shaft 78 of motor 76. Stud 128 is received within a cylindrical boss 130 concentrically aligned with annular gear 126 on disk valve 88, and stud 128 and boss 130 can rotate at different speeds. However, while epicyclic gear 112 rotates on an epicyclic path around the longitudinal axis of motor shaft 78, disk valve 88 is constrained from epicyclic rotation due to the engagement of stud 128 into boss 130. However, second gear portion 122 imparts rotation to disk valve 88 around the longitudinal axis of drive shaft 78 and around stud 128. However, due to the gear ratios (pro-Vide details) rotatable disk valve 88 rotates only once for approximately every 138 rotations of eccentric cam 76. Accordingly, for each rotation of disk valve 88 there are approximately 138 suction strokes of driver arm 68 on pumping diaphragm 60.

Figure 2:
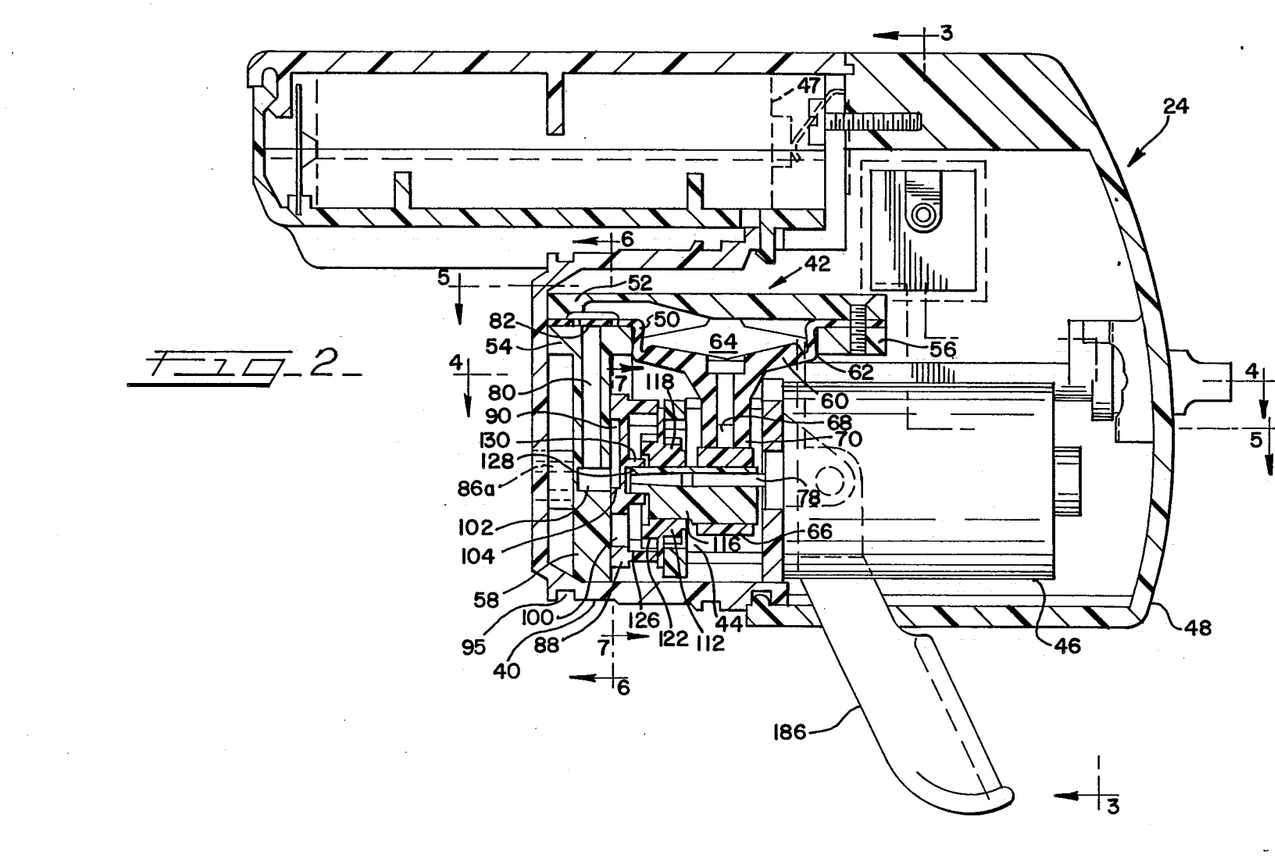
FIG. 2 is a enlarged longitudinal cross-section of the breastpump drive unit of FIG. 1.

As shown in FIGS. 2 and 8, the unit is secured together by screws 130 and 132 that pass through openings 134 and 136 in vertical portion 58 and openings 138 and 140 in stationary gear 120, and are threadably received within openings 142 and 144 in two stationary supports 146 and 148 on motor 46. Thus, suction pump assembly 42 is secured to motor 46, and rotatable valve 88, epicyclic gear 112, stationary gear 120 and driver arm 68 are retained between vertical portion 58 and motor 46.

As shown in FIGS. 6, 7 and B, motor 46 is held in spaced relation to vertical portion 58 by a pair of supports 133 and 135 that extend from the rear surface of vertical portion 58, and supports 146, 148 on motor 46. When assembled, support 133 abuts and is secured to support 146 by fastener 132, and support 135 abuts and is secured to support 148 by screw 130 to hold vertical portion 58 spaced from motor 46 with valve 88, gears 112 and 120, actuator 66 and cam 76 between them.

Figure 4:
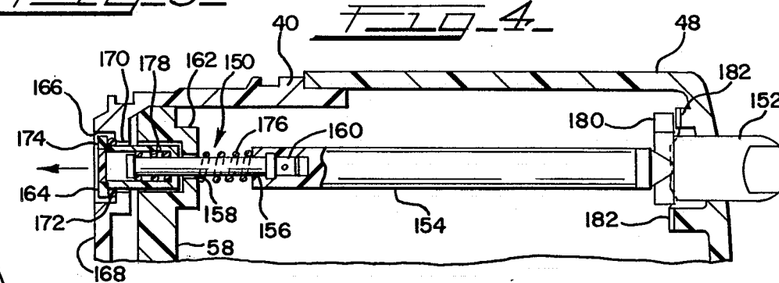
FIG. 4 is a cross-section taken along the plane of line 4—4 of FIG. 2.

As indicated above, the suction drawn on suction valve 22 is regulated by a regulator valve 150 (FIGS. 3, 4 and 6). Regulator 150 includes an adjustment knob 152 that extends outside the housing. Adjustment knob 152 is connected by a rod 154 to a plunger 156 that fits interferingly in a recess 160 at the end of rod 154. Plunger 156 projects through an opening 158 in a recess 162 in vertical portion 58 of membrane deck 54. The end of plunger 156 is received within a cap 164 disposed within a recess 166 on the face 168 of cylindrical end 40 that faces toward suction bell 28. Cap 164 passes through an opening 170 in recess 166 and is received within recess 162 in vertical portion 58.

An O-ring 172 seals between the bottom of recess 166 and an annular flange 174 on cap 164. The strength of the seal formed by O-ring 172 is governed by a spring 178 around plunger 156 biased between the enlarged distal end of plunger 156 and the bottom of the recess within cap 164. As adjustment knob 152 is urged inwardly of housing portion 48, the tension on spring 178 will be eased, relaxing the compression of O-ring 172 between flange 174 and recess 166. This permits a certain amount of the air at atmospheric pressure within housing 48 to be drawn past O-ring 172 and into suction bell 22 when suction is drawn on suction bell 22 by suction drive unit 24.

When adjustment knob 152 is urged outwardly of housing portion 48, it pulls plunger 156 inward into the recess in cap 164, compressing spring 178 and increasing the compression on O-ring 172. This increases the suction drawn on suction bell 22 by allowing less atmospheric air (if any at all) past O-ring 172. In this fashion, the user can adjust the pressure drawn by suction drive unit 24 on the breast.

Knob 152 includes a dog 180 that engages an annular ramp 182 around knob 152 inside housing portion 48. Ramp 182 is of varying thickness such that as knob 152 is rotated, dog 180 will urge knob 152 inwardly of housing 48 as dog 180 is rotated onto a thickened portion of ramp 182. However, as dog 180 is rotated to a thinner section of ramp 182, knob 152 is urged outwardly of housing 48 to increase the compression on O-ring 172. Dog 180 is biased against ramp 182 by spring 176 round plunger 158. Spring 176 is biased between the end of rod 154 and the bottom of recess 162 to bias knob 152 outwardly of housing portion 48 and to bias dog 180 against ramp 182.

Motor 46 is powered by batteries 47 (FIG. 2) in battery compartment 184 (FIG. 1). The power from the batteries is switched on and off by a trigger 186 that is pivotally mounted on arms 188 (FIGS. 3 and 8) extending outwardly from motor 46. When trigger 186 is pulled, it operates an electrical switch (not shown) that establishes or breaks an electrical circuit between the batteries and the motor.

While one embodiment of the present invention is shown, others will become apparent to those of ordinary skill in the art. Such embodiments are included within the scope of the present invention unless the claims that follow expressly state otherwise.

I claim:

1. A pump comprising:
   (a) a suction bell;
   (b) container means in fluid communication with said suction bell for receiving fluid from said suction bell;
   (c) suction pump means in fluid communication with said suction bell and said container means for creating reduced pressures in said suction bell and said container means;
   (d) rotatable valve means for interrupting said fluid communication of said suction pump means with said suction bell and said container means and for exposing said suction bell and said container in alternating fashion to said reduced pressures, and for exposing said suction bell to reduced pressure during the time when said container is atmospheric pressure, and for exposing said container to reduced pressure during the time said bell is at atmospheric pressure; and
   (e) pressure-responsive valve means between said bell and said container that opens when said container pressure is lower than the pressure in said bell.

2. The pump of claim 1 further including electric motor means for operating said suction pump and said rotatable valve.

3. The pump of claim 2 wherein said electric motor means further includes an eccentric cam that drives said rotatable valve.

4. The pump of claim 3 wherein said rotatable valve further includes a rotatable gear to drive said rotatable valve, said rotatable gear having an opening therethrough in which said eccentric cam is disposed, and in which said cam operates to rotate said rotatable gear.

5. The pump of claim 4 wherein said rotatable valve includes an annular gear having a larger diameter than said rotatable gear, said annular gear driveably engaging said rotatable gear.

6. The pump of claim 5 further including a stationary annular gear having a diameter larger than said rotatable gear, said stationary annular gear driveably engaging said rotatable gear to impart epicyclic motion to said rotatable gear.

7. The pump of claim 1 further including a diverter plate having a first passage from said pump means, a second passage in communication with said container, and a third passage in communication with said bell, said rotatable valve operating to divert the suction of said pump through said first passage in an alternating fashion between said second and third passages.

8. The pump of claim 7 wherein said rotatable valve has a recess that establishes communication between said first, and said second and third passages in an alternating fashion as said rotatable valve rotates.

9. The pump of claim 8 wherein said recess has a first arcuate path through which said first and second passages communicate, and a second arcuate path through which said first and third passages communicate, said first arcuate path being shorter than said second arcuate path whereby suction is drawn for a longer time on said bell than on said container during a rotation of said rotatable valve.

10. The pump of claim 3 further including a reciprocating rod actuated by said eccentric cam to drive said pump means.

11. The pump of claim 10 wherein said pump means includes a flexible diaphragm disposed across a pumping chamber, said reciprocating rod actuating said flexible diaphragm.

12. The pump of claim 11 wherein said reciprocating rod is connected to said diaphragm on one end, and includes a passage on the other end to receive said eccentric cam.

13. The pump of claim 12 wherein said eccentric cam includes two eccentric cam surfaces, a first surface that drives said reciprocating rod, and a second surface that drives said rotatable valve.

14. The pump of claim 13 further including an epicyclic gear disposed on said second surface engaging said rotatable valve.

15. The pump of claim 13 wherein said first cam surface has a larger diameter than said second cam surface.

16. The pump of claim 12 wherein said diaphragm includes inlet and outlet valves for said pump chamber.

17. The pump of claim 14 further including a stationary annular gear having a gear diameter larger than the diameter of said epicyclic gear, said epicyclic gear engaging said stationary gear whereby epicyclic motion is imparted to said epicyclic gear.

18. The pump of claim 17 wherein said rotatable valve includes an annular gear, said epicyclic gear engaging said rotatable valve annular gear.

19. The pump of claim 18 wherein said rotatable valve includes a boss, and said eccentric cam includes a stud mounted concentric with the axis of rotation of said eccentric cam, said boss receiving said stud, whereby said epicyclic gear rotates said rotatable valve around said stud.

20. The pump of claim 1 wherein said pressure-responsive valve means includes a flapper valve.

21. A pump comprising:
(a) a suction bell;
(b) a container in fluid communication with said suction bell for receiving fluid from said suction bell;
(c) suction means in fluid communication with said suction bell and said container means for generating a suction in said suction bell and said container means;

(d) motor means for driving said suction means, said motor means including an eccentric cam that rotates about an axis;
(e) a rotatable valve engaging said cam wherein said rotatable valve is rotatable about said axis for interrupting said fluid communication of said suction means with said suction bell and said container and for exposing said suction bell and said container in alternating fashion to said reduced pressures, and for exposing said suction bell to reduced pressure during the time when said container is at atmospheric pressure, and for exposing said container to reduced pressure during the time said bell is at atmospheric pressure;
(f) an epicyclic gear mounted on said eccentric cam, and drivedly engaging said rotatable valve; and
(g) a stationary gear engaged with and imparting epicyclic movement to said epicyclic gear when said cam is rotated by said motor means.

22. The pump of claim 21 further including a diverter plate having a first passage from said pump means, a second passage in communication with said container, and a third passage in communication with said bell, said rotatable valve operating to divert the suction of said pump through said first passage in an alternating fashion between said second and third passages.

23. The pump of claim 21 further including a diverter plate having a first passage from said pump means, a second passage in communication with said container, and a third passage in communication with said bell, said rotatable valve operating to divert the suction of said pump through said first passage in an alternating fashion between said second and third passages.

24. The pump of claim 21 further including a diverter plate having a first passage from said pump means, a second passage in communication with said container, and a third passage in communication with said bell, said rotatable valve operating to divert the suction of said pump through said first passage in an alternating fashion between said second and third passages.

25. The pump of claim 21 further including a diverter plate having a first passage from said pump means, a second passage in communication with said container, and a third passage in communication with said bell, said rotatable valve operating to divert the suction of said pump through said first passage in an alternating fashion between said second and third passages.

26. The pump of claim 21 further including a diverter plate having a first passage from said pump means, a second passage in communication with said container, and a third passage in communication with said bell, said rotatable valve operating to divert the suction of said pump through said first passage in an alternating fashion between said second and third passages.

27. The pump of claim 21 further including a diverter plate having a first passage from said pump means, a second passage in communication with said container, and a third passage in communication with said bell, said rotatable valve operating to divert the suction of said pump through said first passage in an alternating fashion between said second and third passages.

28. The pump of claim 20 further including a regulator valve for regulating the pressure drawn by said suction means on said suction bell.

29. The pump of claim 28 wherein said regulator valve includes a cap, a seal, and biasing means for biasing said cap against said seal, and means for adjusting the bias of said cap against said seal wherein said cap can permit air to be drawn into said bell past said seal when a suction is drawn on said bell.

30. The pump of claim 29 wherein said adjustment means includes a rotatable knob, a dog and an annular ramp on which said dog is engaged whereby the bias of said biasing means can be adjusted by rotation of said knob.

* * * * *

UNITED STATES PATENT AND TRADEMARK OFFICE
CERTIFICATE OF CORRECTION

PATENT NO. : 4,964,851
DATED : October 23, 1990
INVENTOR(S) : Karl O.A.H. Larsson It is certified that error appears in the above-identified patent and that said Letters Patent is hereby corrected as shown below:

In column 5, lines 10 and 11, please delete "proVide" and substitute therefor --provide--.

In column 5, line 26, before "motor" please delete "B" and substitute therefor --8--.

In claim 1, line 16, before "atmospheric" please insert --at--.

Signed and Sealed this

Twentieth Day of July, 1993

Attest:

MICHAEL K. KIRK

Attesting Officer     Acting Commissioner of Patents and Trademarks